United States Patent [19]

Eicken et al.

[11] Patent Number: 5,134,072
[45] Date of Patent: Jul. 28, 1992

[54] PREPARATION OF A WATER-SOLUBLE MODIFIED ENZYME BY COVALENTLY BONDING AN ENZYME TO A POLYURETHANE PRE-POLYMER/BISULFITE ADDUCT

[75] Inventors: Ulrich Eicken, Korschenbroich; Wilhelm Tischer, Peissenberg, both of Fed. Rep. of Germany

[73] Assignee: Boehringer Mannheim GmbH, Mannheim-Waldhof, Fed. Rep. of Germany

[21] Appl. No.: 582,138

[22] Filed: Sep. 13, 1990

Related U.S. Application Data

[63] Continuation of Ser. No. 156,164, Feb. 16, 1988, abandoned.

[30] Foreign Application Priority Data

Feb. 23, 1987 [DE] Fed. Rep. of Germany ....... 3705687

[51] Int. Cl.$^5$ .................. C12N 9/96; C12N 11/08; C12N 9/00
[52] U.S. Cl. .................... 435/188; 435/180; 435/183
[58] Field of Search ............ 435/174, 177, 180, 183, 435/188

[56] References Cited

U.S. PATENT DOCUMENTS

| | | | |
|---|---|---|---|
| 3,984,365 | 10/1976 | Lienert et al. | 528/45 |
| 4,094,744 | 6/1978 | Hartdegen et al. | 195/63 |
| 4,592,957 | 6/1986 | Dahm et al. | 430/138 X |
| 4,734,439 | 3/1988 | Reischl | 521/54 |

FOREIGN PATENT DOCUMENTS 61-081785  4/1986  Japan.
1321352   6/1973  United Kingdom.

OTHER PUBLICATIONS

Petinaux, Marcel, et al., Chemical Abstracts, vol. 87, No. 6645g, p. 20, 1977.
Abstract: Japanese Patent Application 60-232089 (1985) "Method for Immobilizing Biocatalyst...", Cl. C12N 11/04.

Primary Examiner—David M. Naff
Attorney, Agent, or Firm—Felfe & Lynch

[57] ABSTRACT

A water-soluble polyurethane-modified enzyme is prepared by reaction of an enzyme in aqueous solution with an aqueous solution of a water-soluble polyurethane pre-polymer/bisulfite adduct at a pH greater than 7 to covalently bond the enzyme to the adduct. Preferably, a ratio of enzyme to pre-polymer/bisulfite adduct of from 1:10 to 10:1 is used.

13 Claims, No Drawings

PREPARATION OF A WATER-SOLUBLE MODIFIED ENZYME BY COVALENTLY BONDING AN ENZYME TO A POLYURETHANE PRE-POLYMER/BISULFITE ADDUCT

This application is a continuation of application Ser. No. 156,164, filed Feb. 16, 1988, now abandoned.

BACKGROUND OF THE INVENTION

The present invention is concerned with polyurethane-modified, water-soluble enzymes, as well as with a process for the preparation thereof.

It is known to modify proteins, such as enzymes, in order to improve certain properties of the proteins, for example certain physical-chemical properties, such as the solubility in a desired system (for example an analytical reagent), the storage stability, compatability in a hydrophobic medium (for example in the case of binding to synthetic resin surfaces) or the biological properties, such as increasing the half life time of a protein in plasma, the reduction of the antigen action and the activity in a non-aqueous system, especially in an organic solvent.

From Federal Republic of Germany Patent Specification No. 27 55 053, it is known to modify biologically-active proteins by reaction with a urethane polymer. According to this, a biologically-active protein and a liquid polyurethane pre-polymer which is at least dispersable in water are reacted under substantially water-free conditions to give a solution which is then dispersed in water. It is a disadvantage of this process that, for example, the biologically-active protein must be used as a dry powder because otherwise, because of the reactivity of the NCO groups with water, a foam or a highly cross-linked product is formed; furthermore, only pre-polymers can be used which are already water-soluble. In addition, due to the heterogeneous reaction of a water-free protein with the pre-polymer, as a rule the activity is greatly reduced or even completely destroyed.

It is an object of the present invention to provide a polyurethane-modified enzyme, as well as a process for the preparation thereof which avoids the above-mentioned disadvantages and with which a modified enzyme is made available which, in particular, has the desired solubility properties and biological properties and can be obtained with a substantially improved activity yield.

SUMMARY OF THE INVENTION

Thus, according to the present invention, there is provided a polyurethane-modified, water-soluble enzyme which is obtainable by the reaction of an enzyme in aqueous solution with an aqueous solution of a polyurethane pre-polymer/bisulphite adduct at a pH value greater than 7. The addition of an organic solvent which is miscible with water, for example water/dioxan, can possibly be advantageous.

The present invention also provides a process for the preparation of a water-soluble enzyme modified with polyurethane by reaction of an enzyme with a water-soluble polyurethane pre-polymer/bisulphite adduct in aqueous solution at a pH value greater than 7, wherein the enzyme is reacted in aqueous solution with an aqueous solution of the polyurethane pre-polymer/bisulphite adduct.

DETAILED DISCLOSURE

Surprisingly, we have found that, according to the process of the present invention, polyurethane-modified enzymes can be obtained which, in comparison with the polyurethane-modified enzymes known from the prior art, display substantially better activity yields.

The reaction is preferably carried out in such a manner that the aqueous solution of the polyurethane pre-polymer/bisulphite adduct is added to a solution of the enzyme in aqueous buffer with a pH value greater than 7, the reaction preferably being carried out at a pH value greater than 8 and especially at a pH value greater than 9.

Alternatively, the reaction can be carried out in reverse order, namely, the solution of the enzyme is added to the solution of the polyurethane pre-polymer/bisulphite adduct. However, care must hereby be taken that the polymer solution is so chosen that no hydrolysis takes place, for example when the pH is $<7$.

As polyurethane components, there can be used NCO-terminated polyurethane pre-polymers of differing functionality. Monofunctional polyurethanes obtained from a monool and diisocyanate are preferably used for the enzyme modification when a cross-linking is not desired, for example for known, therapeutically used enzymes. Bifunctional polyurethanes obtained by the reaction of diols with a molar excess of diisocyanate have the advantage of great variability of the starting materials, a synthesis according to the modular principle thereby being possible (cf. in this regard, Encyclopedia of Polymer Science and Technology, page 508 et seq.; Ullmann's Encyclopädie der techn. Chemie, Vol. 19, pp. 303–310, pub. Verlag Chemie, 1983). Furthermore, they can easily be worked up since no or little cross-linking of the polymers takes place. In the case of the enzyme modification with these polyurethanes, cross-linked modified enzymes can also be obtained. Polyfunctional polyurethanes, which are obtained by the reaction of polyols and diisocyanates, can be especially advantageous when a cross-linking of the modified enzyme is expressly desired.

The remaining reactive isocyanate groups of the polyurethane pre-polymers are then converted with sodium bisulphite ($NaHSO_3$) into the polyurethane pre-polymer/bisulphite adduct used according to the present invention for the modification. This has the advantage that, due to the introduction of an ionic group, the hydrophilia of the polymers increases so that, even in the non-modified state, water-insoluble polymers can be made water-soluble. Due to the reaction, the reactivity of the NCO groups towards water is reduced, it thereby being possible to protect NCO groups against hydrolysis and further reaction. By choice of the appropriate polyurethane pre-polymers, by means of which cross-linked polymers, hydrophobic-hydrophilic block polymers, as well as a molecular weight modification are possible, the properties of the polyurethane-modified enzymes most preferable for the desired use can be achieved.

The reaction temperature and the pH value of the reaction are to be so chosen that no deactivation (denaturing) of the enzyme takes place. It is preferable to work at ambient temperature although it is also possible to work at elevated temperatures up to the denaturing temperature of the enzyme or with cooling. It is preferred to work at a pH value of from 7 to 10.

The ratio of polyurethane pre-polymer/bisulphite adduct to the enzyme can be so chosen that, after the reaction, still free, not reacted NCO bisulphite adduct groups (carbamoylsulphates) are still present on the polymer. However, too great an excess of free NCO-bisulphite adduct groups should be avoided because otherwise an often undesired chain elongation could take place. In the case of the presence of an excess of free NCO-bisulphite adduct groups, these can, however, be removed by the addition of an additional $NH_2$ group-containing reagent, for example lysine, an undesired chain elongation thereby being avoided. If the number of polymer chains bound to each enzyme molecule is to be reduced, which in certain cases can be preferable, then an excess of enzyme amino groups is used. Depending upon the properties of the particular enzyme, such as solubility, number of amino groups per molecule and the like, and upon the intended purpose of use, as well as upon the properties of the polyurethane pre-polymer/bisulphite adduct, for example the number of reactive groups per gram, there can easily be determined the most preferable ratio, the ratio of the two components preferably being from 10:1 to 1:10.

Polyurethane pre-polymers with at least one and preferably two terminal isocyanate groups, such as are used according to the present invention, are either known or can be synthesised according to known processes. There can be used, for example, all polyurethane pre-polymers known from the prior art for polyurethane-modified proteins (cf. Ullmann, supra) which form a water-soluble bisulphite adduct and do not react further with water. For example, there can be used the non-ionic hydrophilised polyurethane pre-polymers obtained from diisocyanates with polyether polyols, such as are used in Federal Republic of Germany Patent Specification No. 25 43 093 for the preparation of water-soluble bisulphite addition products. Instead of the polyether polyols (cf. Ullmann, supra), there can, however, also be used polyester polyols (cf. Ullmann, supra) with about the same molecular weight. It is also possible to react the polyether polyols or polyester polyols with a higher functional polyisocyanate (cf. Ullmann, supra; for example Desmodur; Bayer). Aliphatic and cycloaliphatic isocyanates are preferred since the bisulphite adducts thereof are more stable than those of the aromatic isocyanates.

As polyurethane pre-polymer components, there are preferably used polyurethane re-polymers which contain an oxyalkylene structure, preferably one of oxyethylene or also especially of oxypropylene and/or oxybutylene units, which are derived from the appropriate polyalkylene glycols, for example polyethylene glycol and preferably polypropylene glycol and/or especially from polybutylene glycol. Block copolymers or statistical co-polymers can thereby also be used, especially those of, for example, ethylene oxide and propylene oxide.

The polyurethane pre-polymers can also have a polyester structure and preferably a linear polyester structure which is especially derived from a polyester diol, for example from a polyester diol from a dibasic acid, especially one with 2 to 6 carbon atoms, and a diol, especially with 2 to 6 carbon atoms and 2 to 6 oxygen atoms, for example triethylene glycol (cf. Ullmann, supra).

Especially preferred according to the present invention are polyurethane pre-polymers which are derived from propylene glycol and especially from ethylene glycol or contain oxypropylene and/or oxyethylene units of at least 10 and especially of 50 mole %.

The numerical value of the molecular weight of the polyalkylene polyols or polyester polyols is preferably of from 500 to 10000 Dalton and especially from 800 to 6000 Dalton and most preferably of from 800 to 2000 Dalton.

In the case of using monools, those are preferably employed in which the second hydroxyl group of the polyalkylene glycol or polyester diol is masked by etherification or esterification, for example by a methyl radical.

As diisocyanate components for the polyurethane pre-polymers, there are preferred aliphatic and cycloaliphatic diisocyanates, for example 1,4-tetramethylene diisocyanate, 1,10-decamethylene diisocyanate, cyclohexylene-1,4-diisocyanate and especially 1,6-hexamethylene diisocyanate. However, there can also be used aromatic diisocyanates, for example toluene-2,6-diisocyanate, or other aromatic diisocyanates normally used for the preparation of polyurethanes.

The preparation of the polyurethane pre-polymer/bisulphite adducts employed according to the present invention can take place in known manner, for example as described in Federal Republic of Germany Patent Specification No. 25 43 093.

As bisulphite components, there can be used salt-like, water-soluble bisulphites, potassium or ammonium bisulphite and especially sodium bisulphite or sodium hydrogen sulphite dissolved in water preferably being used.

The reaction of the polyurethane pre-polymer with the bisulphite compound to give the adduct can be carried out in a purely aqueous system but also in a mixture of water and an organic solvent which is miscible with or soluble in water, for example a mixture of water/dioxan. In this case, a solution of the polyurethane pre-polymer in an organic solvent is preferably mixed with a solution of the bisulphite compound in water. For the purpose of the present invention, it is preferred to remove excess diisocyanate (or polyisocyanate), low molecular weight polyaddition products of low molecular weight reactive NCO-bisulphite adducts and/or unreacted bisulphite compounds, this removal preferably being carried out by dialysis.

As enzymes for the polyurethane-modified enzymes according to the present invention, there can be used all water-soluble enzymes such as are, for example, already known in modified form from the prior art (cf., for example Federal Republic of Germany Patent Specification No. 27 55 053), for example oxido-reductases, lyases, transferases, isomerases, hydrolases, ligases and the like.

The purity of the enzyme is thereby of subsidiary importance for the reaction according to the present invention, i.e. there can be used pure enzymes or impure enzymes, for example in the form of extracts and the like.

The concentrations of polyurethane pre-polymer/bisulphite adduct and enzyme in the aqueous solutions used for the reaction are not critical. The concentration of the polyurethane pre-polymer/bisulphite adduct in the solution is preferably from 0.1 to 25% by weight and especially from 4 to 10% by weight and the concentration of the enzyme is from 0.1 to 5% by weight and especially from 1 to 2% by weight. These concentrations are to be understood to be the concentrations in the solutions before mixing.

The following Examples are given for the purpose of illustrating the present invention; if not stated otherwise, parts and percentages are parts by weight and percentages by weight.

EXAMPLE 1

200 g. water-free polyethylene glycol 2000 (=0.2 mole OH) (obtainable from Merck, Darmstadt) are reacted with 23.5 g. (=0.28 mole NCO) hexamethylene diisocyanate while stirring at 80° C. until the NCO content of the mixture is 1.5% (=0.28 mole NCO). The NCO content is determined by reaction with an excess of di-n-butylamine after back titration with hydrochloric acid against bromophenol blue as indicator. As soon as the desired content of NCO groups is achieved, 100 g. dioxan are added thereto.

40.4 g. of the above-prepared pre-polymer, which corresponds to 10 mM NCO groups, are dissolved in 25 ml. dioxan. 1.05 g. $Na_2S_2O_5$ or an equivalent amount of $NaHSO_3$ is dissolved in 25 ml. water and introduced all at once into the dioxan solution, the solution thereby becoming slightly turbid. The solution is further stirred for 30 minutes at ambient temperature and then introduced into a dialysis tube and dialysed overnight against desalinated water. By means of the dialysis, there are removed, in particular, unreacted $Na_2S_2O_5$ and low molecular weight polyaddition products. After the dialysis, the solution is subjected to lyophilisation, the polymer being obtained as a white powder.

The content of reactive groups can be determined by the method of G. B. Guise (J. Appl. Polymer Sci., 21, 3427/1977). Typically, the values are in the region of 0.05 mM/g.

EXAMPLE 2

20 g. water-free polypropylene glycol 1025 (=0.04 mole OH) (obtained from Merck, Darmstadt) are reacted with 5.4 g. (=0.064 mole NCO) hexamethylene diisocyanate, while stirring at 100° C., until an NCO content of 4% is achieved.

After the addition of 5 g. dioxan, the solution is cooled in an ice-bath to 4° C., 100 ml. cold ethanol are then added thereto and the mixture is stirred until a homogeneous solution is obtained. Immediately thereafter, 2.28 g. $Na_2S_2O_5$ in 25 ml. water are added thereto all at once. The mixture is then stirred for 30 minutes at 4° C. and for 30 minutes at ambient temperature.

The ethanol and dioxan are removed from the mixture and the residue dialysed overnight against desalinated water. The product obtained is thereafter lyophilised, the polymer being obtained as a highly viscous, glass-like liquid.

EXAMPLE 3 a) 46 mg. α-glucosidase (E.C. 3.2.1.20, from yeast, 50 U/mg., measured at 25° C. with maltose as substrate) are dissolved in 3.1 ml. 0.1M potassium phosphate buffer (pH 8.0). 184 mg. of the pre-polymer described in Example 1 are dissolved in 2 ml. water and added to the enzyme solution and the mixture is incubated for 5 hours at ambient temperature. Thereafter, the mixture is dialysed against 30 mM potassium phosphate (pH 6.8). The activity yield is 60%, referred to the initial activity.

b) For comparison, α-glucosidase is treated as above but without the addition of the pre-polymer.

c) In a further comparative experiment, the α-glucosidase is, as described above, incubated with a pre-polymer, the reactive groups of which have been saturated with di-n-butylamine.

The three samples obtained according to 3 a), b) and c) are incubated at 37° C. in 0.1M potassium phosphate buffer (pH 7.2). The enzymes from comparative examples 3 b) and 3 c) thereby become very turbid (the $E_{405}$ increases from 0.205 to 3.3), whereas the enzyme according to the present invention in 3 a) only became slightly turbid (the $E_{405}$ increases from 0.184 to 0.281). The enzyme is thus free of turbidity.

EXAMPLE 4

30 mg. Penicillin G amidase from *Escherichia coli* (E.C. 3.5.1.11, 10 U/mg., measured with penicillin G as substrate at 28° C.) are dissolved in 3 ml. 0.1M triethanolamine buffer (pH 8.5). 120 mg. of the polymer described in Example 1 are dissolved in 3 ml. of the same buffer and added to the enzyme solution. The mixture is incubated at ambient temperature for 5 hours. After completion of the reaction, dialysis is carried out against 30 mM phosphate (pH 7.5) and the product obtained is lyophilised. The activity yield is 57% of the initial activity.

COMPARATIVE EXAMPLE (PROCESS ACCORDING TO FEDERAL REPUBLIC OF GERMANY PATENT SPECIFICATION NO.2755053)

1.5 g. Polyethylene glycol 1500 (=2 mMole OH) and 0.235 g. hexamethylene diisocyanate (HDI; =2.8 mMole NCO) are mixed and reacted at 80° C. until the NCO content is 2%.

To 1 g. of this pre-polymer are then added 200 mg. of the α-glucosidase used in Example 3 (lyophilised), while stirring, and left to stand for 1 hour at ambient temperature in a desiccator. Working up takes place in the manner described in Federal Republic of Germany Patent Specification No. 27 55 053 by introducing the pre-polymer-enzyme mixture into water, optionally with the addition of a tenside, for example Pluronic. After separation of insoluble material by filtration, the enzymatic activity is measured against p-nitrophenyl-α-D-glucopyranoside. The activity found is 2.2% of the activity used. In comparison therewith, the polyurethane-modified α-glucosidase according to the present invention obtained in Example 3 has an activity of 60%.

We claim:

1. A polyurethane-modified enzyme produced by reaction of an enzyme in aqueous solution with an aqueous solution of a water-soluble polyurethane pre-polymer/bisfulite adduct at a pH greater than 7, wherein the ratio of enzyme to pre-polymer bisulfite adduct is from 1:10 to 10:1, and wherein the reaction forms a covalent bond between the enzyme and the pre-polymer/bisulfite adduct.

2. Process for the preparation of a water-soluble enzyme modified with polyurethane which comprises reacting an enzyme with a water-soluble polyurethane pre-polymer/bisulfite adduct in aqueous solution at a pH value greater than 7, wherein the ratio of enzyme to pre-polymer bisulfite adduct is from 1:10 to 10:1, and wherein the reaction forms a covalent bond between the enzyme and the pre-polymer/bisulfite adduct.

3. Process according to claim 2, wherein the aqueous solution of the polyurethane pre-polymer/bisulphite adduct is added to a solution of the enzyme in an aqueous buffer.

4. Process according to claim 2, wherein the pH is greater than 8.

5. Process according to claim 4, wherein the pH is greater than 9.

6. Process according to claim 2, wherein the polyurethane pre-polymer is derived from a polyalkylene glycol or a monoester or monoether thereof.

7. Process according to claim 6, wherein the polyalkylene glycol is a polyethylene glycol, polypropylene glycol or a block co-polymer or a random copolymer of ethylene glycol and propylene glycol.

8. Process according to claim 2, wherein the polyurethane pre-polymer is derived from a polyester diol or a monoester or monoether thereof.

9. Process according to claim 2, wherein the molecular weight of the polyurethane pre-polymer is from 500 to 10000 Dalton.

10. Process according to claim 9, wherein the molecular weight of the polyurethane pre-polymer is from 800 to 2000 Dalton.

11. Process according to claim 2, in which the reaction takes place in a mixture of water and a water-miscible organic solvent.

12. Process according to claim 2, in which the reaction takes place in a mixture of water and a water-soluble organic solvent.

13. Process of claim 2 wherein the reaction takes place in a mixture of water and dioxan.

* * * * *